United States Patent
Koeppel et al.

(10) Patent No.: US 11,709,159 B2
(45) Date of Patent: Jul. 25, 2023

(54) SYNTHETIC AGRICULTURAL SENSOR

(71) Applicant: AquaSys LLC, Washington, DC (US)

(72) Inventors: Adam Koeppel, Washington, DC (US); Tyler Locke, Alexandria, VA (US); Kevin Kelly, Alexandria, VA (US)

(73) Assignee: AQUASYS LLC, Washington, DC (US)

( * ) Notice: Subject to any disclaimer, the term of this patent is extended or adjusted under 35 U.S.C. 154(b) by 0 days.

(21) Appl. No.: 17/466,593

(22) Filed: Sep. 3, 2021

(65) Prior Publication Data

US 2022/0074914 A1 Mar. 10, 2022

Related U.S. Application Data

(60) Provisional application No. 63/074,674, filed on Sep. 4, 2020.

(51) Int. Cl.
| | | |
|---|---|---|
| *G01N 33/24* | (2006.01) | |
| *G06N 3/08* | (2023.01) | |
| *G01N 27/22* | (2006.01) | |
| *G06N 3/044* | (2023.01) | |

(52) U.S. Cl.
CPC .......... *G01N 33/24* (2013.01); *G01N 27/223* (2013.01); *G06N 3/044* (2023.01); *G06N 3/08* (2013.01); *G01N 2033/245* (2013.01)

(58) Field of Classification Search
CPC .............. G01N 2033/245; G01N 33/24; G06N 3/0445; G06N 3/08; G06N 3/044
See application file for complete search history.

(56) References Cited

U.S. PATENT DOCUMENTS

| | | |
|---|---|---|
| 8,731,836 B2 | 5/2014 | Lindores et al. |
| 10,564,122 B1 | 2/2020 | Xu et al. |
| 2010/0014070 A1 | 1/2010 | Bruins et al. |
| 2018/0271015 A1 | 9/2018 | Redden et al. |

(Continued)

FOREIGN PATENT DOCUMENTS

WO 2014107797 7/2014

OTHER PUBLICATIONS

Jimenez et al., A Survey on Intelligent Agents and Multi-Agents for Irrigation Scheduling, Published Online Jul. 23, 2020, Computers and Electronics in Agriculture176, Elsevier B.V., 23 pp. (Year: 2020).*

(Continued)

*Primary Examiner* — Toan M Le
(74) *Attorney, Agent, or Firm* — Hamre, Schumann, Mueller & Larson, P.C.

(57) ABSTRACT

In order to predict plant stresses at a localized level, data feeds from many sensor types can be fused and analyzed to create a synthetic sensor estimating plant water stress, predicting microclimatic conditions, and performing localized plant disease and pest modeling. To make this affordable, an array of low-cost, lower precision sensors can be used. Sensor fusion is used to improve the accuracy of each sensing element by using machine learning to fuse data from the other sensing elements in the array. Additionally, machine learning can create a "synthetic sensor" replicating the output of high-cost and maintenance intensive sensing devices by using machine learning to replicate their output.

10 Claims, 12 Drawing Sheets

(56) References Cited

U.S. PATENT DOCUMENTS

2019/0050948 A1    2/2019  Perry et al.
2019/0246549 A1    8/2019  Peters et al.

OTHER PUBLICATIONS

International Search Report and Written Opinion issued in PCT/US2021/049059, dated Dec. 10, 2021.
Geng et al., "An Agricultural Monitoring System Based on Wireless Sensor and Depth Learning Algorithm", International Journal of Online Engineering, vol. 13, No. 12, 2017, 11 pages.

* cited by examiner

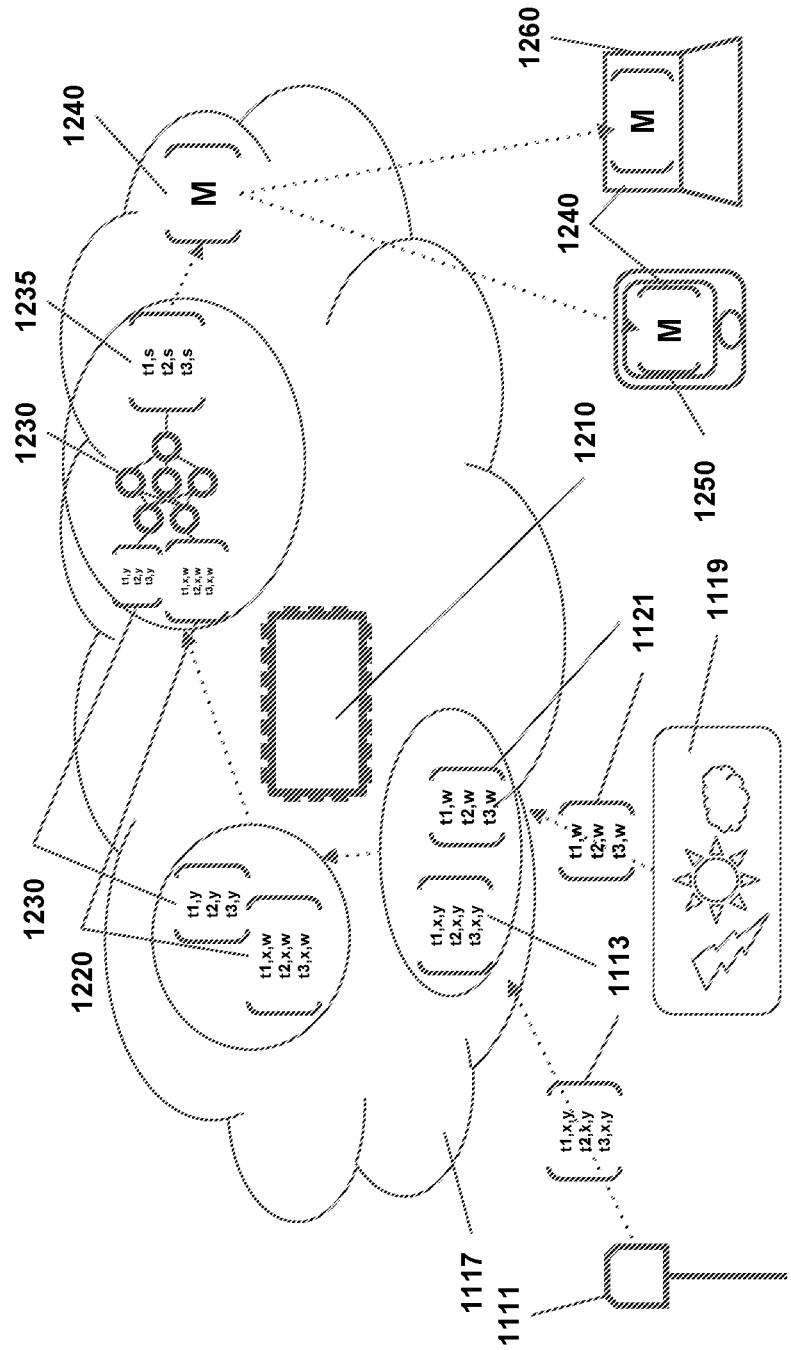

SYNTHETIC AGRICULTURAL SENSOR

The present disclosure relates to monitoring and predicting agricultural performance and in one or more embodiments, to measuring and predicting yield-reducing plant abiotic and biotic stressors, and delivering intervention guidance to farmers or those in the agricultural industry or for geophysical science applications to mitigate these stressors.

BACKGROUND

In order to maximize yields while simultaneously minimizing irrigation water usage, farmers need to understand, predict, and manage plant stressors, which are the yield reducing stresses plants undergo, for example, when plants struggle to draw water or nutrients from the soil, are attacked by diseases or pests, or are environmental stressors like heat waves, droughts, and cold snaps. Currently, there are products available to help farmers or those in the agricultural industry to monitor some of the stresses, for example, products that measure soil conditions or track local weather conditions. The existing products, however, are expensive to purchase and/or expensive to maintain, e.g., initial calibration and continued maintenance and calibration. Additionally, farmers currently must estimate the future plant stress impacts on plant yield, and then guesstimate an input application schedule to reduce the plant stress(es).

SUMMARY

In an embodiment, in order to predict plant stresses at a localized level, many data feeds from many sensor types are fused and analyzed to create a synthetic sensor that can, for example, be used for estimating plant water stress from non-living factors, e.g., abiotic stressors, predicting microclimatic conditions, and performing localized plant disease and pest modeling, e.g., biotic stressors. To make this affordable, in an embodiment, an array of low-cost, lower precision sensors can be used, in which sensor fusion that uses machine learning can be used to improve the accuracy of each sensing element by using machine learning to fuse data from the other sensing elements in the array and/or for creating a "synthetic sensor" that replicates the output of high-cost and maintenance intensive sensing devices which is beneficial for agricultural and geophysical science applications.

According to an embodiment, a method is provided for generating a synthetic sensor for providing an agricultural measurement that includes receiving a plurality of secondary signals from a plurality of secondary sensors; providing the plurality of secondary signals to a neural network including a learning model that transforms the plurality of secondary signals into a value of a primary signal; and transmitting the primary signal from the trained learning model to a device having a display.

According to another embodiment, a system is provided that includes a plurality of secondary sensors configured to output a plurality of secondary signals; a neural network including a learning model that transforms a the plurality of secondary signals into a value of a primary signal; and at least one device having a display that is configured to output the primary signal that is a transformation of the plurality of second signals from the plurality of secondary sensors from the trained learning model.

The various embodiments include at least one of and/or a combination of the following features:

the learning model includes obtaining a measured value of the primary signal from at least one primary sensor, and modifying the learning model based on the measured value of the primary signal;

the neural network is a recurrent neural network that creates the learning model that models a relationship between the plurality of secondary signals and the measured value of the primary signal;

the training of the learning model includes using secondary signals from at least five secondary sensors;

the value of the primary signal is not a value measured by the plurality of secondary sensors.

the primary signal replaces one of the plurality of secondary signals;

at least one historical environmental data value, in which a future value of the primary signal is predicted based on the at least one historical environmental data value;

the at least one historical environmental data value is weather data;

the plurality of secondary sensors is used to measure at least one of soil volumetric moisture, soil tension, soil temperature, air humidity, air temperature, and barometric pressure, and the primary signal is a value for soil matric potential.

BRIEF DESCRIPTION OF THE DRAWINGS

In the detailed description that follows, embodiments are described as illustrations only since various changes and modifications will become apparent to those skilled in the art from the following detailed description. The use of the same reference numbers in different figures indicates similar or identical items.

FIG. 12 is a schematic representation of the machine learning model to create a synthetic sensor for sensing soil-atmosphere gas flux, in accordance with at least some embodiments described herein.

DETAILED DESCRIPTION

Figure 1:
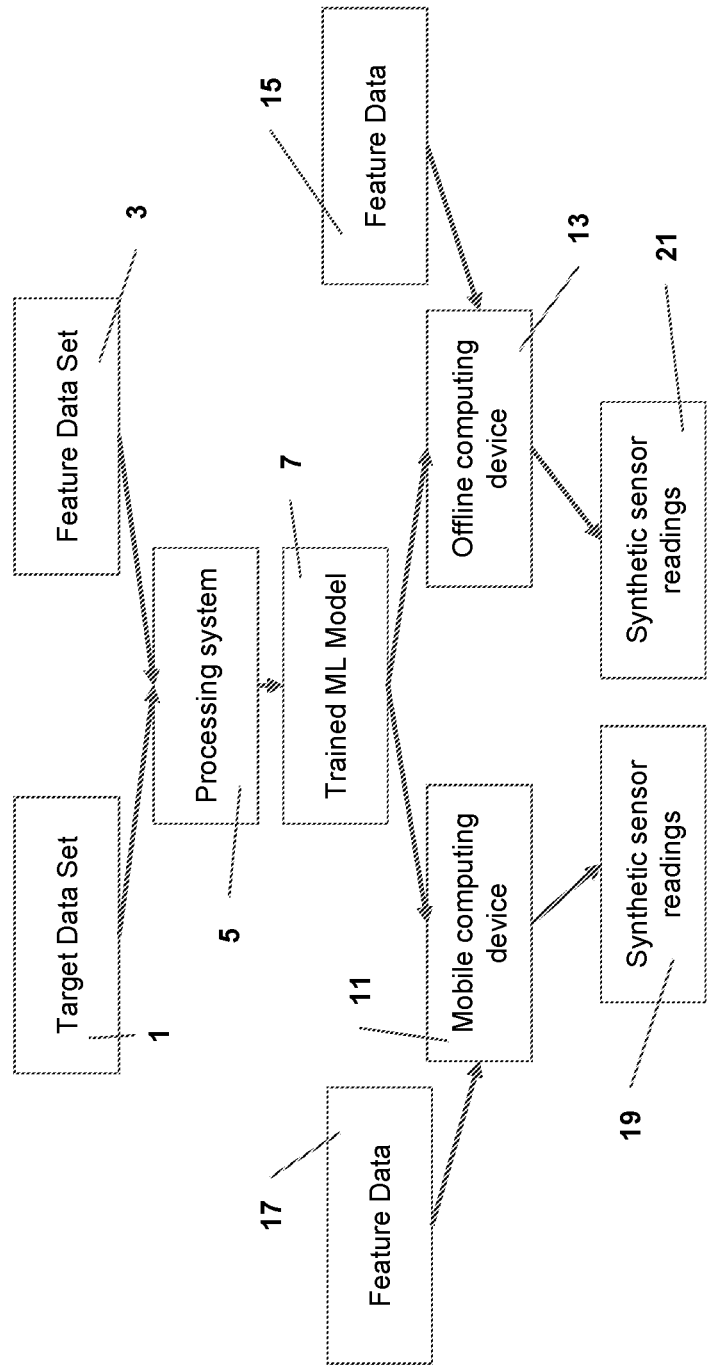
FIG. 1 shows an example process flow diagram in which a synthetic sensor system can be implemented, in accordance with at least some embodiments described herein.

In the following detailed description, reference is made to the accompanying drawings, which form a part of the description. In the drawings, similar symbols typically identify similar components, unless context dictates otherwise. Furthermore, unless otherwise noted, the description of each successive drawing may reference features from one or more of the previous drawings to provide clearer context and a more substantive explanation of the current example embodiment. Still, the example embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein and illustrated in the drawings, may be arranged, substituted, combined, separated, and designed in a wide variety of different configurations, all of which are explicitly contemplated herein.

Currently no technology exists that can affordably and accurately measure, monitor, and model localized plant stresses.

Machine learning driven sensor fusion overcomes this deficiency and also provide two advantageous approaches superior to traditional direct sensing devices. In an embodiment, machine learning driven sensor fusion can create "synthetic sensors" that replicate the performance of an expensive, maintenance prone, or difficult to install sensor, without requiring the presence or continuous presence of that sensor. In another embodiment, machine learning driven sensor fusion can be used to improve the accuracy and/or precision of any single sensor reading with an array of sensors that measure signals that are related to each other, as further discussed below. Accordingly, the synthetic sensor allows accurate forecasting of plant stress(es) to provide farmers with the ability to, among other things, confidently irrigate, apply inputs to crops with the precise amount and timing needed to eliminate plant stress, avoid the environmental damage of over application, and increase crop yields while reducing water, fertilizer, and spray applications, and other means for reducing the effect of the plant stress on the plant.

In an embodiment, the synthetic sensor is particularly suitable to provide an affordable soil sensing approach. It is appreciated that many discrete soil conditions are interrelated. For example, soil moisture measurements and trends can be related to soil conductivity which can be related to soil matric potential which can be related to soil temperature. In addition, these measurements can be related to above ground micro-climatic measurements, for example, air humidity and air temperature. These measurements can also be related to past weather conditions, including temperature and precipitation.

In an embodiment, in order to replicate a high performance (high accuracy, high precision) but affordable sensor for providing an agricultural measurement, for example, a single soil measurement, a synthetic sensor is provided. In this embodiment, at least two data sets can be used for creating the synthetic sensor signal. For example, one data set can include primary signals from a primary sensor, which can be, for example, a signal from a very high quality sensor. It is appreciated that a "high quality sensor" can be a laboratory or research instrument that typically requires a combination of calibration by a manufacturing technician during manufacturing, installation in the field by a person with technical qualifications, and periodic maintenance and calibration in the field. These high quality sensors provide excellent accuracy and precision, but have high cost of purchase, and high cost of operation due to the physical components involved in manufacture, and the human intervention needed to produce, calibrate, and operate them.

Another data set can include a plurality of secondary signals from a plurality of secondary sensors, which can be signals from an array of lower quality, lower cost, and lower performance sensors. In an embodiment, the plurality of sensors can include at least three sensors in an array, and preferably, at least five sensors in the array. It is appreciated that the "lower quality sensors" can be consumer electronics components used in common devices found in homes and businesses, such as, for example, surface mount printed circuit board sensors, for example, temperature sensors in thermostats, gas sensors in smoke detectors, or capacitive touch sensors used for input controls in devices, such as hand held devices and computers, digital thermometers, relative humidity sensors, cost capacitive soil moisture sensor, based on a printed circuit board and a low frequency oscillating crystal, an ultra low cost soil conductivity sensor, based on resistance pads on a PCB, a low cost, uncalibrated soil tension sensor based on the architecture of the low cost capacitive soil moisture sensor, a barometric pressure sensor, a soil surface infrared temperature sensor. By providing the plurality of secondary signals to a neural network that includes a learning model, the machine learning driven sensor fusion can use the plurality of signals from the lower quality sensors to generate the readings of a primary signal, for example, a signal from the very high quality sensor, without relying on the continued use of the very high quality sensor. This is explained further in the following embodiments.

It is appreciated that multiple approaches can be used to create the machine learning models. For example, in an embodiment, the modeling uses a simple linear regression. A linear regression model defines the linear relationship between the feature and target datasets. While this type of model is typically used for a single feature and target application, synthetic sensor feature datasets can represent multiple measurements from disparate sensors at a regular interval on a contiguous timescale.

In another embodiment, a Recurrent Neural Network (RNN) is used for the modeling. The RNN is designed to use sequence data and is capable of accepting a multivariate input dataset, which can be used to define both linear and non-linear relationships. One problem with RNNs, however, is gradient vanishing in which the effect is that some long-term dependencies are lost during training. Thus, in a preferred embodiment, the modeling includes using a specialized RNN called Long Short-Term Memory (LSTM). An LSTM preserves dependencies that have a small but important effect on the accuracy of the model. It is appreciated that the present disclosure is not limited to machine learning approaches using LSTM, RNNs, or any other established model, but more generally related to models that allow sensor fusion based on machine learning applied to signals from sensor arrays.

For example, in an embodiment, the synthetic sensor is used to generate a measurement of soil matric potential, since soil matric potential sensing is typically expensive, both in the cost of the physical devices, and the labor necessary to maintain them. Additionally, these sensors often require manual calibration in a lab prior to installation in the field, and ongoing calibrations in the field, to maintain accuracy and precision, especially as changing environmental conditions affect readings. Thus, the synthetic sensor for soil matric potential can be used to accurately provide this measurement without needing the expensive hardware or labor which is beneficial for agricultural and geophysical science applications.

In this embodiment, the synthetic sensor is created by obtaining measurements to create a target data set of time series data for a particular geographical location and soil depth using a high quality (and therefore high cost) soil matric potential sensor. Examples of high quality soil matric potential sensors include those manufactured by, for example, Meter Group (e.g., Teros 21), Decagon (e.g., MPS-2, MPS-6), Spectrum Technologies (e.g., Watermark Soil Moisture Sensor), Irrometer (e.g., Irrometer and Watermark Sensors), Ecomatik (e.g., SMT100), Blumat (e.g., PRO plus), and other manufacturers. The target data set can be transferred, for example, to a cloud computing storage and processing facility for safekeeping and neural network training.

At the same geographical location and soil depth of the soil matric potential sensor, an array of low cost sensors is simultaneously installed to generate a first feature data set, which can include production soil data set of time series data. The production soil data set can also be transferred, for example, to a cloud computing storage and processing facility for safekeeping and neural network training. The soil data sensor array includes a plurality of sensors, for example, a low cost capacitive soil moisture sensor, based on a printed circuit board and a low frequency oscillating crystal, an ultra low cost soil conductivity sensor, based on resistance pads on a PCB, low cost soil temperature sensor, based on a moisture resistant potted surface mount PCB temperature sensor, a low cost, uncalibrated soil tension sensor based on the architecture of the low cost capacitive soil moisture sensor mentioned above, but with an appropriate buffer applied over the capacitive sensor area, and combinations thereof.

Further, at the same geographical location, but above the soil surface, an array of low cost sensors can also be simultaneously installed to generate second feature data set that includes a production micro climate data set of time series data. This micro climate feature data set can be transferred to a cloud computing storage and processing facility for safekeeping and neural network training. This microclimate feature data sensor array could include a plurality of sensors, for example, an air humidity sensor, an air temperature sensor, a barometric pressure sensor, a soil surface infrared temperature sensor, and combinations thereof.

Still further, at the same geographical location, or at the closest available geographical location, at least one historical environmental data, for example, weather feature data stream of time series data can be gathered as a third feature data set, from either a local weather station, or from a weather service. The feature weather data set can be stored in a cloud computing storage and processing facility for safekeeping and neural network training. The feature weather data can include: air temperature, air humidity, recorded precipitation, dew point, UV Index, solar radiation, cloud cover percentage, barometric pressure, and combinations thereof.

The cloud computing storage and processing facility is a processing system that includes computing devices and processors that are used to train a recurrent neural network (RNN) to create a machine learning (ML) model for soil matric potential based on the target data set and at least one of or some combination of the first, second, and third feature data sets. Training a RNN to create an ML model is generally a computationally intensive process so it is performed at the cloud computing facility in which computational resources, e.g., a plurality of computing devices and/or processors, and energy are abundant. While each individual data collected in the first, second, and third feature data sets listed above, taken alone, is not sufficient to accurately and precisely determine to soil matric potential, it is appreciated that each individual data can directly or indirectly influence soil matric potential. As a result, the RNN is able to accurately and precisely convert data from the feature data set into data signal for a synthetic sensor that provides a reading of soil water potential, even though no soil water potential sensor data is included in any of the feature data sets.

A number of factors contribute to the machine learning model's overall efficacy. To be successful, a model needs to be both accurate and broadly applicable. Using the right architecture for the problem, optimizing its hyper parameters, and choosing the right "stopping point" during model training, which all factor into how well the model performs. Similarly, having the right inputs, or features, has an outsized impact on model performance. A model can be trained with an indefinite number of features that describe in very high detail the environment in which the particular sensor array is in. To make the model accurate it is trained with only those feature datasets that contribute positively to its error rate. Thus, optimizing the model for a particular target output, means being selective about what information is fed into it during the training phase. It is known, for example, that soil moisture is highly correlated with soil water potential. Thus, soil moisture is a good candidate for inclusion as a feature dataset in a model with soil water potential as its target output. By contrast, air-quality datasets are not likely to contribute positively to the performance of a soil water potential model.

The way to determine if a particular dataset contributes positively to the model's performance can be by calculating the model's error. If a model has lower error (and therefore better performance) when a feature is included vs excluded, the dataset is deemed worthy of inclusion in the training phase. This process of adding and removing features is automated via a scripting language that iteratively compares the model performance with and without a particular feature, and can relatively quickly narrow the list of features for inclusion in the final training phase of model.

The modeling to the target data set can be considered complete and be used as a machine learning model for the synthetic sensor, when the error of the modeling reaches a predetermined error rate, e.g., between 90%-99% accuracy or 1%-10% error threshold, and preferably between 90-95% accuracy or 5-10% error threshold. Error is calculated by comparing the model's accuracy against a known target dataset, with lower error being better. To make the model broadly applicable and not overfitted for one particular dataset, transfer learning adapts a model previously trained on a single dataset to generalize across several disparate datasets that each can be unique in geographic location, soil type, ambient environment, etc.

The trained ML model can be used for a synthetic sensor for generating a data signal for soil matric potential. In an embodiment, the ML model can be transmitted from the cloud computing storage and processing facility. The ML model can then be stored on computer readable medium as a software application, which when executed by a processor, transforms a data feed from at least one feature data set into an output that takes the form of a data feed equivalent to the target data set, e.g., a data signal for a primary sensor, such as, the soil matric sensor. Since execution of the ML model is a much less computationally intensive process, the storage and execution of the ML model can be performed on an individual personal computer, a tablet computer, or a mobile computer like a smartphone or other processor-driven device. This can also be performed on small embedded systems that use microcontrollers, such as a sensor having a display that is located at the same geographical location as the secondary sensors.

For example, in an embodiment, an agronomist working on an irrigated orchard or vineyard can download the ML model for the synthetic sensor into a mobile software application on a mobile device, in which the agronomist can use the software application, along with a feature data sets from the feature data sensor array, and feature weather data from a weather service to generate synthetic sensor readings of soil matric potential. The agronomist can then use the synthetic sensor readings of soil matric potential to determine a deficit irrigation strategy based on soil matric potential thresholds, in which irrigation events are triggered by reaching a level of soil matric potential that corresponds to a water deficit that balances the productivity and quality of the output of the vineyard or orchard against water availability and cost. Alternatively, the machine learning model could be downloaded to a software application accessible on a computing device, or a mobile computing device, or embedded into a display built into a sensor in the sensor array. The device using the machine learning model only needs access to the feature data from the data sensor array, for example, by Bluetooth, Wi-Fi, RFID, wired connection, or combinations thereof, but not a network connection, to generate the synthetic sensor measurements.

Accordingly, since the ML model is downloaded to a local device, the agronomist can continue receiving synthetic sensor readings of soil matric potential after removing the soil matric potential sensors, since the soil matric potential sensors were used to generate the target data that was used to train the ML model. In fact, it is appreciated that, when the ML model is based on a suitably diverse sample of multiple soil types, the agronomist can receive synthetic sensor readings of soil matric potential even without ever needing to install a high cost soil matric potential sensor at a particular geographical location.

In an another embodiment, machine learning driven sensor fusion can be used to improve the accuracy and precision of at least one individual reading from within an array of sensors each sensing related signals, since many discrete soil conditions can be interrelated. For example, soil moisture measurements and trends relate to soil conductivity which can relate to soil matric potential which can relate to soil temperature. In addition, these measurements can also relate to above ground micro-climatic measurements like air humidity and air temperature and can also be related to past weather conditions, including ambient temperature and precipitation.

In order to improve the performance (for example, higher accuracy, higher precision) of a single soil measurement, a machine learning driven sensor fusion approach can use at least two data sets. A target data set is generated by a very high quality sensor. A feature data set is generated by an array of a plurality of lower quality, lower cost, and lower performance sensors, including a lower quality, lower cost, and lower performance version of the previously mentioned very high quality sensor. Machine learning driven sensor fusion is then used to improve the accuracy of at least one of the lower quality, lower cost, and lower performance versions of the very high quality sensor using the plurality of signals from the lower quality sensors, by generating or creating a measurement value that is similar to a measurement provided by the very high quality sensor, as further discussed below.

For example, in an embodiment, the synthetic sensor is used to generate measurement values of soil volumetric moisture and soil conductivity, since volumetric moisture and soil conductivity sensing are typically expensive due to the high cost of the devices and the systems necessary to power them. For example, traditional devices attempt to achieve a very large "area of influence" to measure a large soil volume, for a better representative reading, such readings, however, require large and expensive sensing elements, and more power to drive the sensing elements. Additionally, these sensors often require manual calibration in a lab prior to installation in the field, and ongoing calibrations in the field, to maintain accuracy and precision, especially as changing environmental conditions affect readings. Thus, using the synthetic sensor that uses the machine learning driven sensor fusion approach that accurately provides such measurements without requiring the expensive hardware or labor is beneficial for agricultural and geophysical science applications.

In this embodiment, the synthetic sensor is created by obtaining measurements to create a target data set of times series data for a particular geographic location and soil depth using a high quality (and therefore high cost) soil volumetric moisture sensor and a similarly high quality (and therefore high cost) soil conductivity sensor. Examples of high quality soil volumetric moisture and soil conductivity sensors include those manufactured by: Meter Group (e.g., Teros sensors), Decagon (e.g., EC-5 probes), Campbell Scientific (e.g., CS600 series), Irrometer (e.g., Watermark and IRROMETER), Extech (e.g., DO700, DO610, EC600, MO750, etc.), Davis (e.g., Vantage Pro2™ and Environ-Montior®), Sentek (e.g., EnviroSCAN), and other manufacturers. This target data set can be transferred, for example, to a cloud computing storage and processing facility for safekeeping and neural network training.

At the same geographical location and soil depth, an array of a plurality of low cost sensors is simultaneously installed to generate a first feature data set, which can include a production soil data set of time series data. The production soil data set can also be transferred to, for example, a cloud computing storage and processing facility for safekeeping and neural network training. This soil feature data sensor array includes a plurality of sensors, for example, a low cost capacitive soil moisture sensor, for example a printed circuit board and a low frequency oscillating crystal, a ultra low cost soil conductivity sensor, for example resistance pads on a PCB, a low cost soil temperature sensor, for example a moisture resistant potted surface mount PCB temperature sensors, a low cost, uncalibrated soil tension sensor based on the architecture of the low cost capacitive soil moisture sensor mentioned above, but with an appropriate buffer applied over the capacitive sensor area, and combinations thereof.

Further, at this same geographical location, but above the soil surface, an array of a plurality of low cost sensors can also be simultaneously installed to generate a second feature data set that includes a production micro climate data set of time series data. The micro climate feature data set can be transferred to a cloud computing storage and processing facility for safekeeping and neural network training. This microclimate feature data sensor array includes a plurality of sensors, for example, an air humidity sensor, an air temperature sensor, a barometric pressure sensor, a soil surface infrared temperature sensor, and combinations thereof.

Still further, at this same geographical location, or at the closest available geographical location, a weather feature data stream of time series data can be gathered as a third feature data set, from either a local weather station, or from a weather service. The feature weather data set can be transferred to and stored in a cloud computing storage and processing facility for safekeeping and neural network training. The feature weather data can include: air temperature, air humidity, recorded precipitation, dew point, UV Index, solar radiation, cloud cover percentage, barometric pressure, and combinations thereof.

The cloud computing storage and processing facility is a processing system that includes, for example, a distributed hardware system, that includes a plurality of networked computing devices and processors that can be used to train a recurrent neural network (RNN) to create two machine learning models, for example, ML models for soil volumetric moisture and for soil conductivity, based on the target data set and at least one of or some combination of the first, second, and third feature data sets. In an embodiment, the RNN which is a multivariate "many-to-one" Long-Short-Term-Memory (LSTM) architecture is used for the ML model. Training a RNN to create an ML model is generally a computationally intensive process so it is performed at the cloud computing facility in which computational resources, e.g., a plurality of computing devices and/or processors, and energy are abundant. While each individual data collected in the first, second, and third feature data sets from the sensors or data streams, taken alone, is not sufficient to accurately and precisely determine soil volumetric moisture and/or soil conductivity, it is appreciated that each measured data source directly or indirectly influences soil volumetric moisture and soil conductivity. As a result, each RNN is able to accurately and precisely convert data from the feature data set into a higher accuracy, higher precision respective reading of soil volumetric moisture or soil conductivity, that is similar to the measurement performance of the high quality soil volumetric moisture sensor and the high quality soil conductivity sensor.

A number of factors contribute to the machine learning model's overall efficacy. To be successful, a model needs to be both accurate and broadly applicable. Using the right architecture for the problem, optimizing its hyper parameters, and choosing the right "stopping point" during model training all factor into how well a model performs. Similarly, having the right inputs, or features, has an outsized impact on model performance. A model can be trained with an indefinite number of features that describe in very high detail the environment in which the particular sensor array is in. To make the model accurate, it is trained with only those feature datasets that contribute positively to its error rate. Thus, optimizing a model for a particular target output means being selective about what information is fed into it during the training phase. It is known, for example, that soil moisture measured by a small field of influence capacitive soil sensor is highly correlated with soil volumetric moisture. Thus, soil moisture is a good candidate for inclusion as a feature dataset in a model with high accuracy and high precision soil moisture as its target output. By contrast, air-quality datasets are not likely to contribute positively to the performance of a soil water potential model.

The way to determine if a particular dataset contributes positively to the model's performance can be by calculating the model's error. If a model has lower error (and therefore better performance) when a feature is included instead of excluded, it is deemed worthy of inclusion in the training phase. The process of adding and removing features is automated via a scripting language that iteratively compares the model performance with and without a particular feature, and can relatively quickly narrow the list of features for inclusion in the final training phase of the model.

The modeling to the target data set can be considered complete and be used as a machine learning model for the synthetic sensor, when the error of the modeling reaches a predetermined error rate, e.g., between 90%-99% accuracy or 1%-10% error threshold, and preferably between 90-95% accuracy or 5-10% error threshold. Error is calculated by comparing the model's accuracy against a known target dataset, with lower error being better. To make the model broadly applicable and not overfitted for one particular dataset, transfer learning adapts a model previously trained on a single dataset to generalize across several disparate datasets that each can be unique in geographic location, soil type, ambient environment, etc.

The trained ML models can be used for a synthetic sensors(s) for generating data signals for soil volumetric moisture sensing and the soil conductivity sensing. In an embodiment, the ML model can be transmitted from the cloud computing storage and processing facility. The ML models can then be stored on computer readable medium as a software application, which when executed by a processor, transforms a data feed from at least one feature data set into an output that takes the form of a data feed equivalent to the target data set, e.g., a data signal for a primary sensor, such as, the soil volumetric moisture sensor and/or the soil conductivity sensor. Since execution of the ML models is a much less computationally intensive process, the storage and execution of the ML models can be performed on an individual personal computer, a tablet computer, or a mobile computer like a smartphone, or other processor-driven device. This can also be performed on small embedded systems that use microcontrollers, such as sensors having a display that is located at the same geographical location as the secondary sensors.

For example, in an embodiment, an agronomist working on an irrigated orchard or vineyard can download the ML models for the synthetic sensors to a mobile software application on a mobile device, in which the mobile application will store the ML model(s) on computer storage media that can include volatile and nonvolatile, removable and non-removable media implemented in any method or technology for storage of information, such as computer readable instructions, data structures, program modules, or other data, and use it, when executed by a processor, with at least one of the feature data set(s) from the feature data sensor arrays, and the feature weather data from a weather service to generate synthetic sensor readings of soil volumetric moisture and soil conductivity. The agronomist can then use the synthetic sensor readings of soil volumetric moisture, accessible on a computing device, or a mobile computing device, or embedded into the feature data sensor array, to determine optimal irrigation set durations to ensure enough water has been applied to the orchard or vineyard to avoid excessive plant water stress between irrigation events. The agronomist can use the synthetic sensor reading of soil conductivity to monitor the drawdown of nitrogen fertilizer in the soil of the orchard or vineyard and schedule future applications of fertilizer to maintain agricultural productivity, and avoid over application of nitrogen fertilizer and the associated issues of runoff and water contamination, or gasification and air quality reduction. Accordingly, since the ML models are downloaded to a local device, the agronomist can receive synthetic sensor readings of soil volumetric moisture and soil conductivity even after removing the high quality soil volumetric moisture and conductivity sensors. In fact, it is appreciated that when the ML models are based on a suitably diverse sample of multiple soil types, the agronomist can receive these synthetic sensor readings of soil matric potential without ever needing to install a high cost soil volumetric moisture sensor and/or a soil conductivity sensor.

In addition to creating synthetic sensors, or replicating the performance of high quality expensive sensors with low-cost sensors, in an embodiment, machine learning driven sensor fusion can be used to create accurate predictions and forecasts of future conditions. Predictions need the addition of a production weather forecast data set from a weather forecasting service. For example, at the same geographical location as the target data set and feature data set discussed in the previous embodiments, or at the closest available geographical location, a weather forecast feature data stream of time series data can be gathered from a weather forecasting service. The production weather forecasting data set can be transferred to and stored in, for example, a cloud computing storage and processing facility for safekeeping and neural network training. This production weather forecasting data could include: Air temperature forecasts, Air humidity forecasts, Precipitation forecasts, Dew point forecasts, UV Index forecasts, Solar radiation forecasts, Cloud cover percentage forecasts, Barometric pressure forecasts, and combinations thereof.

The cloud computing storage and processing facility is a processing system that includes computing devices and processors that are used to train a recurrent neural network (RNN), or enhance via transfer learning an existing recurrent neural network using the weather forecast feature data sets. The RNN can be used to incorporate the relationship between forecasted weather data, actual feature data, and synthetic sensor readings to create predictions for soil conditions and microclimatic conditions. Over time, the RNN can incorporate continuous transfer learning to tune to the microclimate at the specific geographical location and improve the accuracy of predictions. The ML model resulting from training with the feature and target datasets can be considered a "translation" model. For example, the ML model takes features as inputs and translates them into the target dataset: A+B=C, in which A is weather data for which the model has both historical and forecast datasets, B is a previously measured value, for example, soil moisture, for which the model has only historical data, and C is a dataset forecast (C(f)), in which the model first forecasts the value of B. This requires an additional model that takes A(h+f) and B(h) as inputs and computes B(f), in which h subscript denotes historical and f denotes forecast data. The resulting datasets A(f)+(B(f) are complete and will produce C(f) when passed through the translation model.

The ML model can be used for a synthetic sensor for predicting a measurement value, for example, soil matric potential. In an embodiment, the ML model can be transmitted from the cloud computing storage and processing facility. The ML model can then be stored on computer readable medium as a software application, which when executed by a processor, transforms a data feed from at least one feature data set into an output that takes the form of a data feed equivalent to the target data set, e.g., a data signal for a primary sensor, such as, the soil matric sensor. Since execution of the ML model is a much less computationally intensive process, the storage and execution of the ML model can be performed on an individual personal computer, a tablet computer, or a mobile computer like a smartphone. This can also be performed on small embedded systems that use microcontrollers, such as a sensor having a display that is located at the same geographical location as the secondary sensors.

For example, in an embodiment, an agronomist working on an irrigated orchard or vineyard can download the ML model for the synthetic sensor to a software application on a mobile device, in which the agronomist can use the mobile software application, along with the feature data set(s) from the feature data sensor array, and/or feature weather data from a weather service to create predictions of future soil matric potential levels. The agronomist can then use the synthetic sensor readings, accessible on a computing device, or a mobile computing device, or embedded into a display on the feature data sensor array, of soil matric potential to precisely schedule irrigation sets before soil matric potential thresholds are reached by programming an irrigation controller. In addition, a software application could use the ML model to automatically send an irrigation schedule to an irrigation controller to automatically pursue a deficit irrigation schedule established by the agronomist. Accordingly, since the ML model is downloaded to a local device, the agronomist or the software application can continue receiving synthetic sensor predictions of soil matric potential even after removing the soil matric potential sensors used to generate the target data that was used to train the ML model. In fact, it is appreciated that when the ML model is based on a suitably diverse sample of multiple soil types, the agronomist or the software application can receive these synthetic sensor readings of soil matric potential even without ever needing to install a high cost soil matric potential sensor.

In yet another embodiment, machine learning driven sensor fusion can also be used for sensing unknown signals. For example, wildfire smoke can taint wine grapes while they are growing in a vineyard and ruin wine produced from these grapes with an ashtray-like smoke taste. While academic studies have identified that exposure to wildfire smoke causes this smoke taint, the exact smoke, microclimate, and even soil conditions necessary for smoke taint to occur are unknown. The only reliable ways to detect smoke taint is to send individual wine grapes to a lab for expensive testing, or to ferment the grapes (a time consuming and expensive process) and taste the resulting wine. Thus, the machine learning driven sensor fusion approach that accurately predicts the likelihood of smoke taint in wine is needed in the wine grape industry. To implement this approach, the array of the plurality of soil and microclimate sensors that produce time series feature data at the specific geographic location mentioned above can be expanded to include an array of a plurality of air sensors that generate time series air quality data that can be transferred to a cloud computing storage and processing facility for safekeeping and neural network training. The sensors can include a volatile organic compound sensor, for example the type typically used to assess indoor air quality, a fine particle sensor, for example the type typically used to generate PM1, PM2.5 and PM10 counts to determine outdoor Air Quality Index, a smoke sensor, for example the type typically used in indoor smoke detectors, a NO sensor, for example the type typically used to determine outdoor Air Quality Index, a NO2 sensor, for example the type typically used to determine outdoor Air Quality Index, an Ozone sensor, for example the type typically used to determine outdoor Air Quality Index, a CO2 sensor, for example the type typically used to assess indoor air quality, a CO sensor, for example the type typically used in indoor smoke detectors, and any other possible air quality sensor or combination thereof.

In this embodiment, it is appreciated that some of the above sensors may be unnecessary, since the relationship between the target data and the feature data is not yet known. In an embodiment, the target data set can be created by periodically harvesting and laboratory testing grapes from the specific geographic location mentioned above, to create a time series data set of smoke taint. Additionally, grapes can be periodically tested and microfermented, to create an additional time series data set of smoke taint. Once sufficient data is gathered, the target data sets for smoke taint and the multiple feature data sets can be used to train a recurrent neural network (RNN) to create a machine learning model for smoke taint prediction. After the creation of the RNN, a sensitivity analysis can be performed on the sensors within the soil, microclimate, and air quality sensor arrays to determine which sensors contribute to an accurate prediction of smoke taint. A systematic statistical approach for a sensitivity analysis can consist of retraining the RNN with a different subset of feature data for each training. After each successive iteration of model training, each model's performance is determined by calculating the error against a known test dataset. Datasets/features input to the model that are highly correlated with the target dataset will reduce the model error, while features that have little or no correlation will contribute to increasing the error. By adding and removing the available datasets to train the model, a systematic statistical approach can be used to find the datasets that correlate to optimum model performance. The sensors that do not contribute significantly to the prediction of smoke taint can then be removed from the feature data sensor array. The trained ML model can be used for a synthetic sensor for predicting, for example, wine grape smoke taint. In an embodiment, the ML model can be transmitted from the cloud computing storage and processing facility. The ML model can then be stored on computer readable medium as a software application, which when executed by a processor, transforms a data feed in the form of the previously mentioned feature data set into an output that takes the form of a data feed equivalent to the target data set. Since execution of the ML model is a much less computationally intensive process, the storage and execution of the ML model can be performed on an individual personal computer, a tablet computer, or a mobile computer like a smartphone, or other processor driven device. This can also be performed on small embedded systems that use microcontrollers.

For example, in an embodiment, a viticulturist working on a vineyard in an area prone to wildfires can receive the ML model for the synthetic sensor on a mobile device, in which the viticulturist can use the mobile application along with a feature data sets from the feature data sensor array, and feature weather data from a weather service to create estimates of the level of smoke taint in the wine grapes. The viticulturist can then use the synthetic sensor estimates of smoke taint, accessible on a computing device, or a mobile computing device, or embedded into a display on the feature data sensor array, to precisely target expensive follow up tests like laboratory testing or micro ferments. As techniques to reduce the effects of wildfire smoke on wine grapes are introduced, the viticulturist can use these estimates to plan applications of smoke taint mitigating processes and materials like new sprays or alternative irrigation strategies that foster vine dormancy during periods of high smoke taint threat. As the models improve with time, the viticulturist may no longer need to employ laboratory testing or microferments and instead be able to use the synthetic sensor output to plan for harvesting and wine production, including wine making strategies to blend away possible smoke taint.

In yet another embodiment, machine learning driven sensor fusion can be used for sensing soil-atmospheric gas flux, which is typically expensive, both in the cost of the physical devices, and the labor necessary to maintain them. An example would be an eddy covariance gas sensor which is a large and expensive device that consumes significant electrical power as well as gas from gas bottles for operation. A typical cost for a complete eddy covariance system is on the order of US $50,000. Examples of eddy covariance gas flux sensors include those manufactured by: Campbell Scientific (e.g., CPEC200, Easy Flux® DL), Los Gatos Research (911-0010, FGGA-24EP), and other manufacturers. Additionally, these gas flux sensors often require manual calibration in a lab prior to installation in the field, and ongoing supply of consumable gases and calibrations in the field, to maintain accuracy and precision, especially as changing environmental conditions affect readings. Thus, a synthetic sensor for soil-atmospheric gas flux that accurately provides measurement without requiring the expensive hardware, consumables, or labor is desired for agricultural and geophysical science applications, since it would enable performance based greenhouse gas credit creation.

The synthetic sensor is created by obtaining measurements to create a target data set of time series data for a particular geographical location using a high quality (and therefore high cost) soil-atmosphere gas flux sensor like an eddy covariance sensor. The target data set can be transferred to, for example, a cloud computing storage and processing facility for safekeeping and neural network training.

At this same geographical location, an array of a plurality of low cost sensors is simultaneously installed at the soil-atmosphere interface to generate a first feature data set, which can include a production soil data set of time series data. The production soil data set can be transferred to, for example, a cloud computing storage and processing facility for safekeeping and neural network training. The soil feature data sensor array can include a nondispersive infrared Carbon Dioxide sensor, a shielded nondispersive infrared Carbon Dioxide sensor, an electrochemical Nitrogen Dioxide sensor, a shielded electrochemical Nitrogen Dioxide sensor, an electrochemical Nitric Oxide sensor, a shielded Nitric Oxide sensor, an electrochemical methane sensor, a shielded electrochemical sensor, and combinations thereof.

Further, at this same geographical location, but above the soil-atmosphere interface, an array of a plurality of low cost sensors is simultaneously installed to generate a second feature data set, which can include a production micro climate and gas data set of time series data. The micro climate feature data set can be transferred to a cloud computing storage and processing facility for safekeeping and neural network training. The microclimate feature data sensor array could include an air humidity sensor, an air temperature sensor, a barometric pressure sensor, a Volatile Organic Compound sensor, a nondispersive infrared Carbon Dioxide sensor, an electrochemical Nitrogen Dioxide sensor, an electrochemical Nitric Oxide sensor, an electrochemical methane sensor, and combinations thereof.

Still further, at this same geographical location, or at the closest available geographical location, a third feature data set can be generated, which can include weather feature data stream of time series data, from either a local weather station, or from a weather service. The feature weather data set can be stored in a cloud computing storage and processing facility for safekeeping and neural network training. The feature weather data could include: Air temperature, Air humidity, Recorded precipitation, Dew point, UV Index, Solar radiation, Cloud cover percentage, Barometric pressure, and combinations thereof.

The cloud computing storage and processing facility is a processing system that includes computing devices and processor that can be used to train a recurrent neural network (RNN) to create a machine learning model for soil-atmosphere gas flux based on the target data set and the multiple feature data sets. While each of the sensors or data streams in the feature data sets, taken alone, is not sufficient to accurately and precisely determine to soil-atmosphere gas flux, each measured or generated value is understood to directly or indirectly influences soil-atmosphere gas flux. As a result, the RNN is able of accurately and precisely convert data from the feature data set(s) into data signals for the synthetic sensor to generate readings of soil-atmosphere gas flux, even though soil-atmosphere gas flux sensor data is not included in the feature data set.

A number of factors contribute to the machine learning model's overall efficacy. To be successful, a model needs to be both accurate and broadly applicable. To make the model accurate, it is trained with only those feature datasets that contribute positively to its error rate. Error is calculated by comparing the model's accuracy against a known target dataset, with lower error being better. To make the model broadly applicable and not overfitted for one particular dataset, transfer learning adapts a model previously trained on a single dataset to generalize across several disparate datasets that each can be unique in geographic location, soil type, ambient environment, etc.

The trained ML model can be used for a synthetic sensor for generating a data signal for soil-atmosphere gas flux. In an embodiment, the ML model can be transmitted from the cloud computing storage and processing facility. The ML model can then be stored on computer readable medium as a software application, which when executed by a processor, transforms a data feed in the form of the previously mentioned feature data set into an output that takes the form of a data feed equivalent to the target data set. This is a much less computationally intensive process, and can be performed on an individual personal computer, a tablet computer, or a mobile computer like a smartphone. Since execution of the ML model is a much less computationally intensive process, the storage and execution of the ML model can be performed on an individual personal computer, a tablet computer, or a mobile computer like a smartphone. This can also be performed on small embedded systems that use microcontrollers, such as a sensor having a display that is located at the same geographical location as the secondary sensors.

For example, in an embodiment, an agronomist working on an orchard or vineyard can download the ML model for the synthetic sensor to a software application on a mobile device, in which the agronomist can use the mobile application, along with a feature data sets from the feature data sensor array, and feature weather data from a weather service to create synthetic sensor readings of soil-atmosphere gas flux. The agronomist can then use the synthetic sensor readings of soil-atmosphere gas flux, accessible on a computing device, or a mobile computing device, or embedded into a display on the feature data sensor array, to pursue and improve a greenhouse gas emissions reduction strategy and generate performance quantified carbon credits.

Accordingly, since the ML model is downloaded to a local device, the agronomist can continue receiving synthetic sensor readings of soil-atmosphere gas flux even after removing the eddy covariance sensors used to generate the target data. In fact, it is appreciated that, when the ML model is based on a suitably diverse sample of multiple soil types, the agronomist can receive these synthetic sensor readings of soil-atmosphere gas flux even without ever needing to install a high cost, high maintenance eddy covariance soil-atmosphere gas flux sensing system.

Further embodiments and examples are provided below.

FIG. 1 illustrates a flowchart that provides an overview of a configuration in which an embodiment of the synthetic sensor may be implemented. A target data set 1, generated by a high cost sensor, and a feature data set 3, generated by an array of low cost sensors are supplied to a processing system 5, which uses the data sets to train a machine learning model 7. The machine learning model 7 is can be transmitted and downloaded to a mobile computing device 11 which is also configured to receive a set of feature data 17 either identical to or different from the feature data set 3. The mobile computing device 11 can then use the machine learning model 7 to compute a synthetic sensor reading that is equivalent to, in accuracy, to the target data 1 using the feature data 17. Alternatively, the machine learning model 7 can be supplied to an offline computing device 13 without a network connection to the original processing system 5, for example, an irrigation controller in an orchard, which also configured receives a set of feature data 15, e.g., via Bluetooth, Wi-Fi, RFID, wired connection to a controller, etc. This offline computing device 13 can then use the machine learning model 7 to compute a synthetic sensor reading with the feature data 15 it has access to offline. The offline computing device 13 includes a processor or microprocessor, which can include a controller and controller software, for example, irrigation controllers and/or software, such as from, Netafim (e.g., NetBeat™, NetMCU™, NMC-Pro, NMC-Junior, NMC-Pro Climate), Jain (e.g., ETwater, Jain Logien™), Galcon (e.g., Galileo Cloud System, GSI Pro, Galileo System, GSI AG series, GSI Gardening, 6000, 7000, and 8000 series), Irritron, Hunter (e.g., X-Core®, X2™, PRO-C®, ICC2, I-Core®, ACC series, HC and HPC series), and Rainbird (e.g., ESP series, for example, ESP-LXIVM, ESP-LXD series, ESP-LXME, ESP-SE3 series, TBOS-BT, LNK), can then use the synthetic sensor reading to make irrigation threshold decisions.

Figure 2:
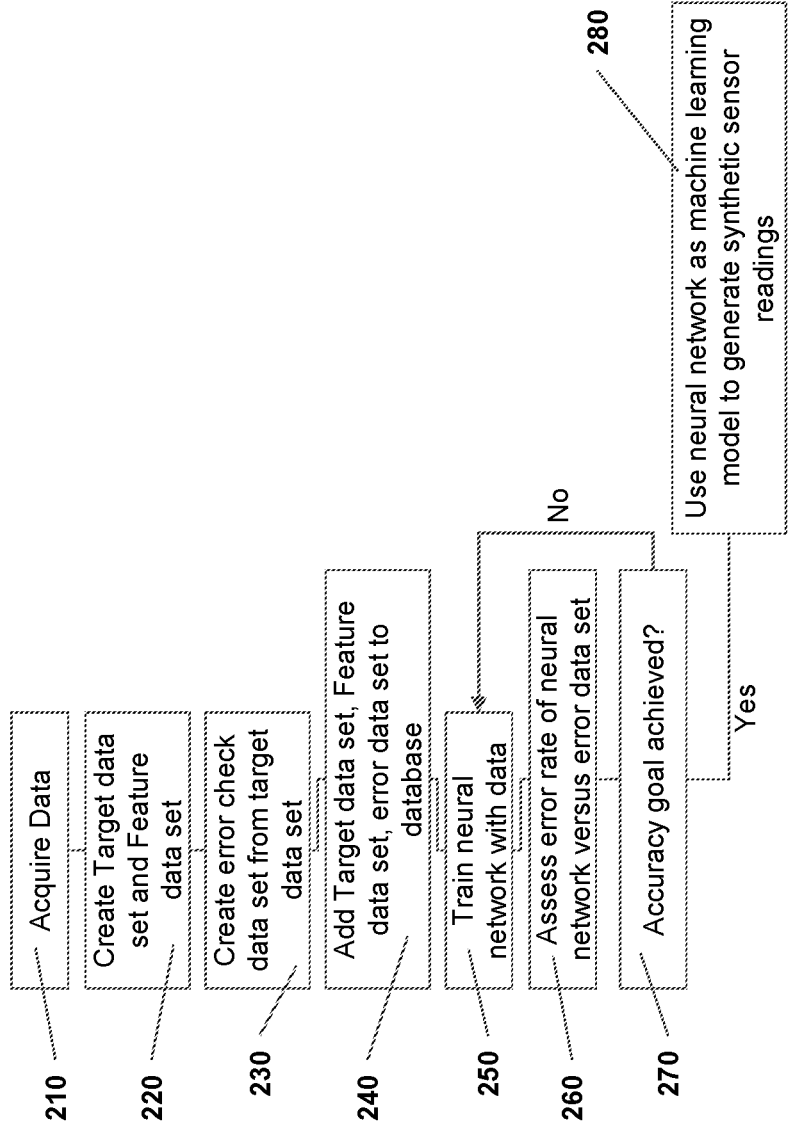
FIG. 2 shows an example process flow diagram in which a synthetic sensor system reading can be obtained, in accordance with at least some embodiments described herein.

FIG. 2 illustrates a flow chart that provides an overview of an algorithm for developing a synthetic sensor, in an embodiment. The algorithm can acquire data at 210, which is then split at 220 into a target data set and a feature data set. The target data set is then split again at 230 to create an error check data set. All three data sets are then added to a database at 240. A neural network is then trained with the data at 250, and the neural network accuracy is checked by comparing the output of the neural network to the error check data set at 260. If the accuracy goal of the neural network is achieved at 270 then the network can be used to generate synthetic sensor readings at 280, and if not the neural network is rejected and returned for retraining at 250.

Figure 3:
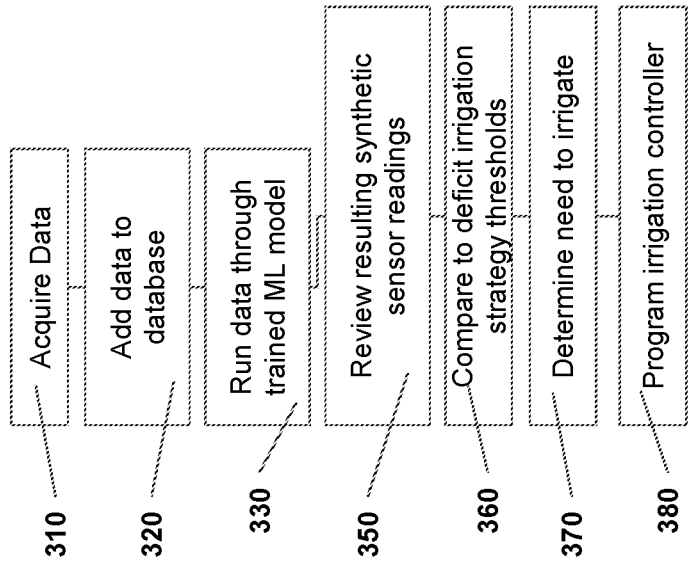
FIG. 3 shows an example process flow diagram illustrating the usage of a synthetic sensor system to make an agronomic decision regarding irrigation, in accordance with at least some embodiments described herein.

FIG. 3 shows a flow chart of how an agronomist or viticulturist would use a synthetic sensor system to determine an irrigation decision. First, the agronomist or viticulturist would acquire data at 310. This could be from an automatic data feed like an Application Programming Interface, or by manually retrieving data from data loggers in the field, or even by reading analog or mechanical sensors. The agronomist or viticulturist would then add this data to a database at 320 by either using an application that automatically adds this data to a database, or by manual entry, as appropriate. The trained machine learning model for the synthetic sensor will then run the data through the trained ML model at 330 in order to generate synthetic sensor data for the agronomist or viticulturist to review at 350. This review could happen on a computing device display, a print out, an interactive audio system, or any other appropriate system for conveying information. The agronomist or viticulturist could then compare the synthetic sensor readings to a deficit irrigation strategy threshold at 360 to determine a need to irrigate 370. Finally, based on the readings and comparisons, the agronomist or viticulturist could then program an irrigation controller at 380.

Figure 4:
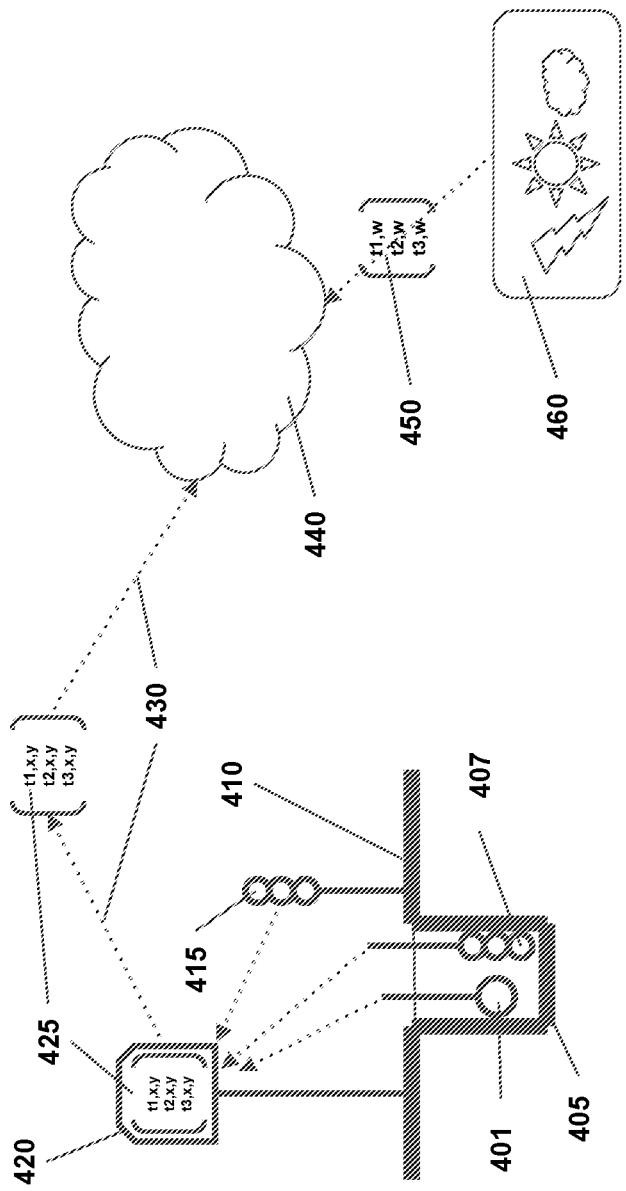
FIG. 4 is a schematic representation for data acquisition to create a synthetic sensor of soil matric potential, in accordance with at least some embodiments described herein.

FIG. 4 illustrates an embodiment in which the data acquisition portion of a machine learning driven sensor fusion system is implemented to create a synthetic sensor of soil matric potential. For example, a high quality, high cost soil matric potential sensor 401 is installed in a borehole 405 at a specific geographical location 410. An array of soil sensors 407 can be installed in this same borehole 405 at the same specific geographical location 410. Above this borehole 405 at the same specific geographical location 410 an array of microclimate sensors 415 can be installed. A data transfer device 420 gathers the time series sensor reading data 425 from the soil matric potential sensor 401, array of soil sensors 407, and the array of microclimate sensors 415. This data transfer device 420 then transfers the time series sensor reading data 425 via a network 430 to a cloud computing storage and processing facility 440. A weather data service 460 provides a feed of time series weather data 450 for the specific geographic location 410 to the cloud computing storage and processing facility 400.

Figure 5:
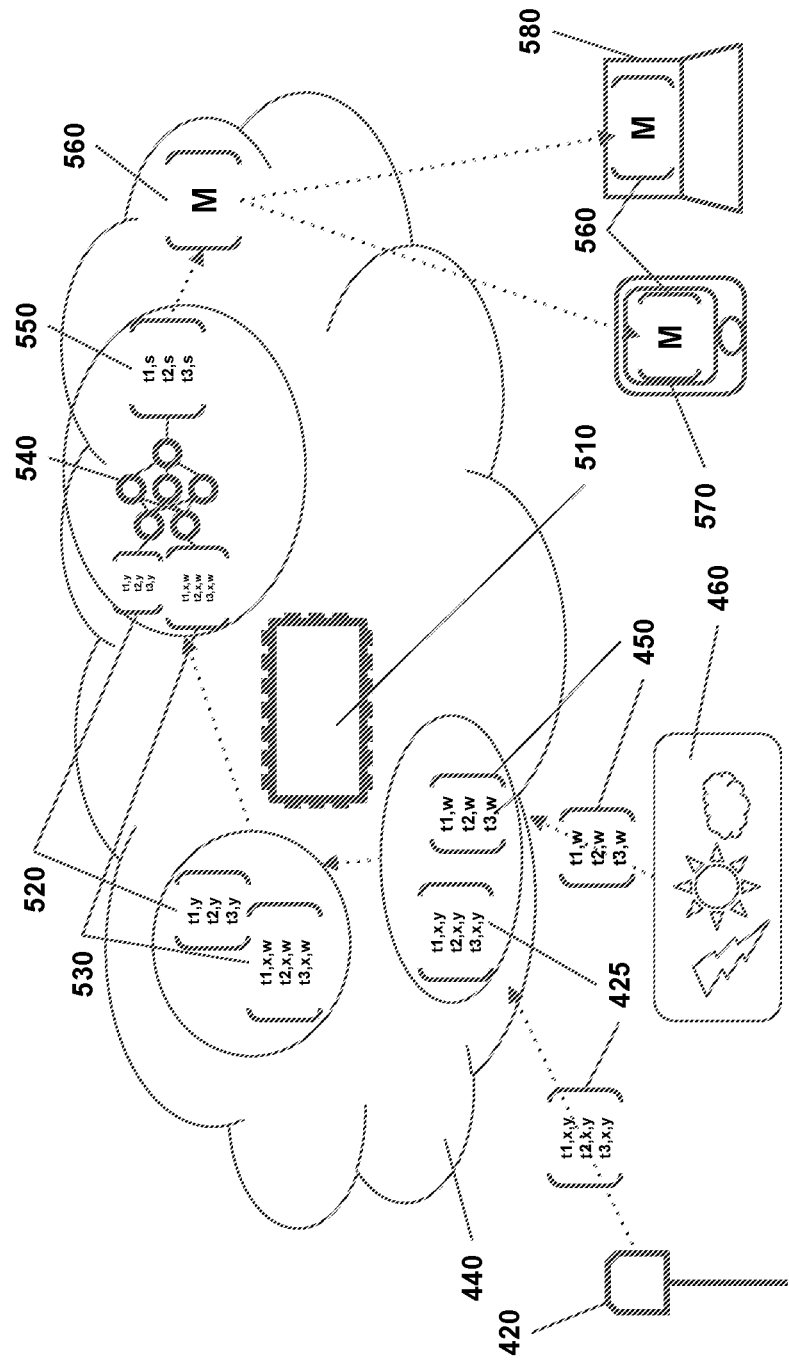
FIG. 5 is a schematic representation of the machine learning model to create a synthetic sensor of soil matric potential, in accordance with at least some embodiments described herein.

FIG. 5 shows an embodiment of the machine learning model creation portion of the machine learning driven sensor fusion system to create a synthetic sensor of soil matric potential. For example, at a cloud computing storage and processing facility 440, the cloud computing system 510 receives the time series sensor reading data 425 from the data transfer device 420. The cloud computing system 510 also receives the time series weather data 450 from the weather data service 460. The cloud computing system then separates the time series data sensor readings 425 into a target data set 520 of time series soil matric potential sensor readings and a feature data set 530 of time series soil array sensor data readings and time series microclimate array sensor data readings. The time series weather data 450 is then added to the feature data set 530 to create a complete feature data set. The target data set 520 and the feature data set 530 are then used to train a neural network 540 to create a machine learning model 550 for soil matric potential. This machine learning model 550 can now create synthetic sensor readings for soil matric potential 560, just using the time series data contained in the feature data set 530. The machine learning model 550 can then be moved out of the cloud computing system 510 and run on another device, including a mobile device 570 or offline computer 580 that has access to a feature data set 530. An agronomist or viticulturist could then use the mobile device to view synthetic sensor readings to make agronomic decisions, or an offline computer could generate synthetic sensor readings to make automated agricultural decisions.

Figure 6:
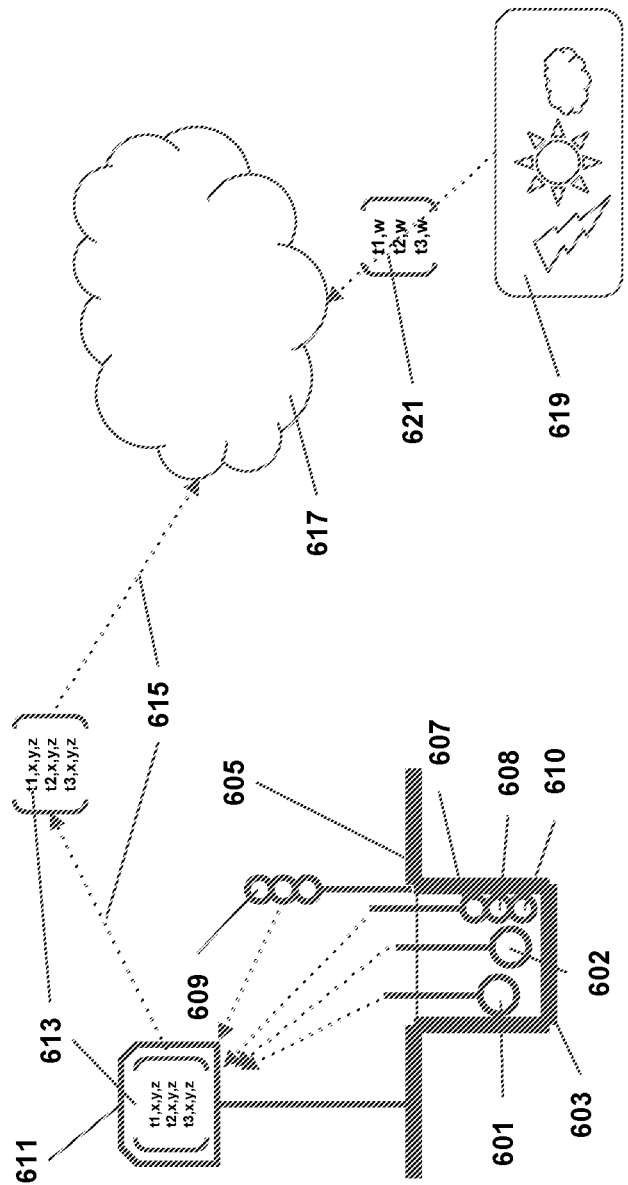
FIG. 6 is a schematic representation for data acquisition to create a synthetic sensor using a sensor array, in accordance with at least some embodiments described herein.

In FIG. 6, the data acquisition portion of a machine learning driven sensor fusion system is implemented, in an embodiment, to replicate the performance, specifically the accuracy and the precision of high quality and high cost sensors with a low cost sensor array having a plurality of low cost sensors. A high quality, high cost soil volumetric moisture sensor 601 is installed in a borehole 603 at a specific geographical location 605. A high quality, high cost soil conductivity sensor 602 is installed in a borehole 603 at a specific geographical location 605. An array of soil sensors 607 including a low cost, low accuracy, uncalibrated soil volumetric moisture sensor 608, and a low cost, low accuracy soil conductivity sensor 610, is also installed in this same borehole 603 at this same specific geographical location 605. Above this borehole 603 at this same specific geographical location 605 an array of microclimate sensors 609 is installed. A data transfer device 611 gathers the time series sensor reading data 613 from the soil volumetric moisture sensor 601, the soil conductivity sensor 602, the array of soil sensors 607, and the array of microclimate sensors 609. This data transfer device 611 then transfers the time series sensor reading data 613 via a network 615 to a cloud computing storage and processing facility 617. A weather data service 619 provides a feed of time series weather data 621 for the specific geographic location 605 to the cloud computing storage and processing facility 617.

Figure 7:
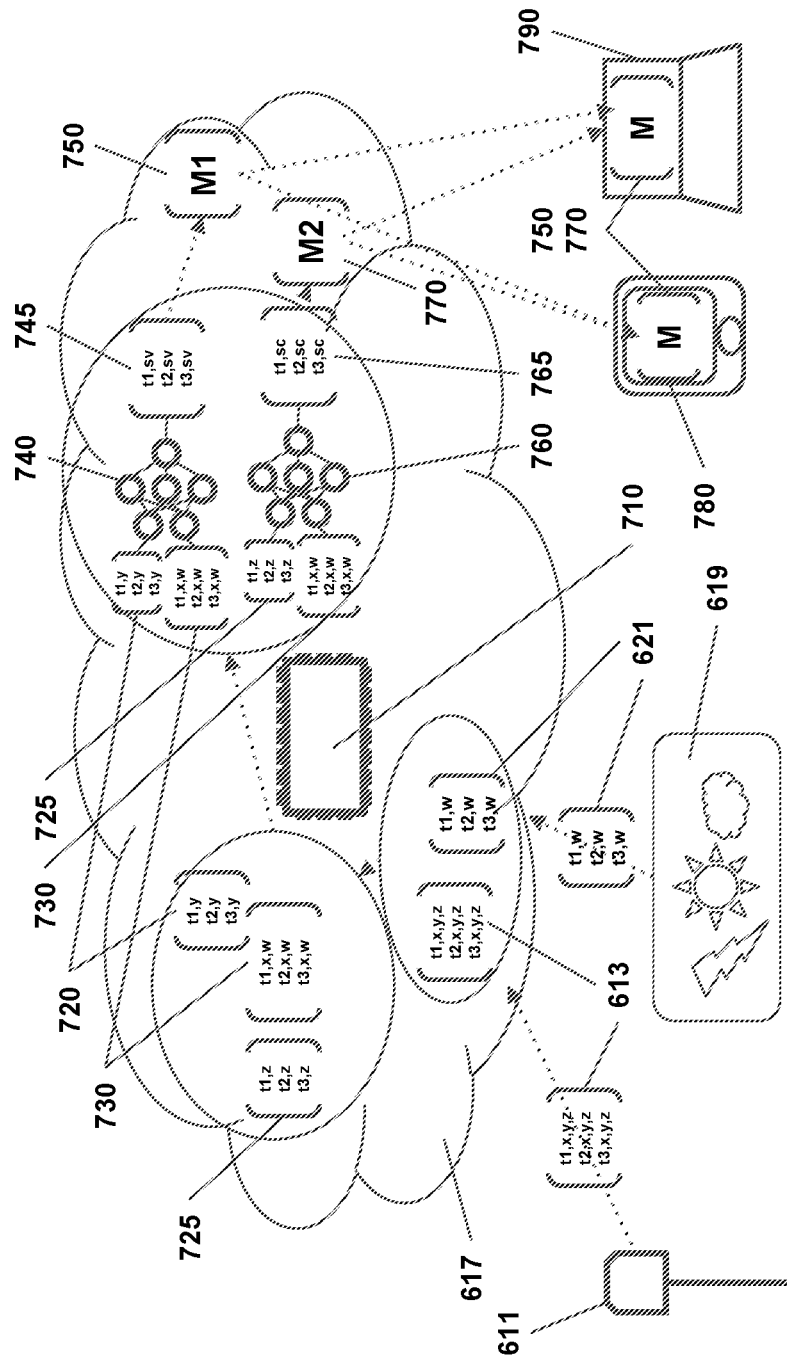
FIG. 7 is a schematic representation of the machine learning model to create a synthetic sensor using a low cost sensor array, in accordance with at least some embodiments described herein.

In FIG. 7, the machine learning model creation portion of a machine learning driven sensor fusion system, in an embodiment, is implemented to replicate the performance, specifically the accuracy and the precision of high quality and high cost sensors with a low cost sensor array. At a cloud computing storage and processing facility 617, the cloud computing system 710 receives the time series sensor reading data 613 from the data transfer device 611. The cloud computing system 710 also receives the time series weather data 621 from the weather data service 619. The cloud computing system then separates the time series data sensor readings 613 into a target data set 720 of time series soil volumetric moisture sensor readings, a target data set 725 of time series soil conductivity sensor readings, and a feature data set 730 of time series soil array sensor data readings and time series microclimate array sensor data readings. The time series weather data 621 is then added to the feature data set 730 to create a complete feature data set. The target data set 720 and the feature data set 730 are then used to train a neural network 740 to create a machine learning model 745 for soil volumetric moisture. This machine learning model 745 can now create synthetic sensor readings for soil volumetric moisture 750, just using the time series data contained in the feature data set 730. The target data set 725 and the feature data set 730 are then used to train a neural network 760 to create a machine learning model 765 for soil conductivity. This machine learning model 765 can now create synthetic sensor readings for soil conductivity 770, just using the time series data contained in the feature data set 730. The machine learning models 745 and 765 can then be moved out of the cloud computing system 710 and run on another device, including a mobile device 780 or offline computer 790 that has access to a feature data set 730. An agronomist or viticulturist could then use the mobile device to view synthetic sensor readings to make agronomic decisions, or an offline computer could generate synthetic sensor readings to make automated agricultural decisions.

Figure 8:
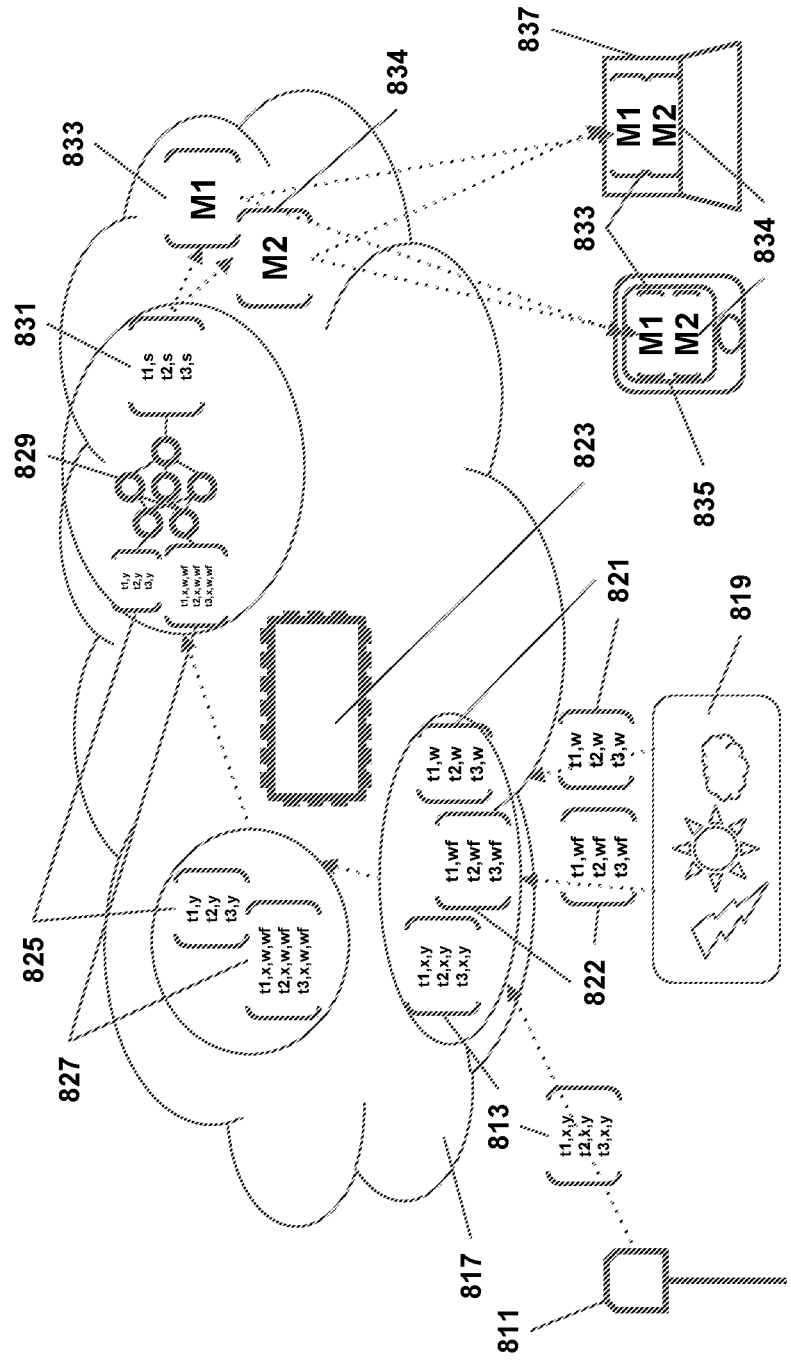
FIG. 8 is a schematic representation of the machine learning model to create a predictive synthetic sensor, in accordance with at least some embodiments described herein.

In FIG. 8, the machine learning model creation portion of a machine learning driven sensor fusion system to create a predictive synthetic sensor is implemented, in an embodiment. At a cloud computing storage and processing facility 817, the cloud computing system 823 receives the time series sensor reading data 813 from the data transfer device 811. The cloud computing system 823 also receives the time series weather data 821 and time series weather forecasts 822 from the weather data service 819. The cloud computing system then separates the time series data sensor readings 813 into a target data set 825 of time series soil matric potential sensor readings and a feature data set 827 of time series soil array sensor data readings and time series microclimate array sensor data readings. The time series weather data 821 and time series weather forecast data 822 is then added to the feature data set 827 to create a complete feature data set. The target data set 825 and the feature data set 827 are then used to train a neural network 829 to create a machine learning model 831 for forecasting soil matric potential. This machine learning model 831 can now create synthetic sensor readings for soil matric potential 833, or synthetic sensor forecasts for soil matric potential 834 just using the time series data contained in the feature data set 827. The machine learning mode 831 can then be moved out of the cloud computing system 823 and run on another device, including a mobile device 835 or offline computer 837 that has access to a feature data set 827. An agronomist or viticulturist could then use the mobile device to view synthetic sensor predictions to plan future agronomic decisions, or an offline computer could generate synthetic predictions to make plan or sequence automated agricultural decisions.

Figure 9:
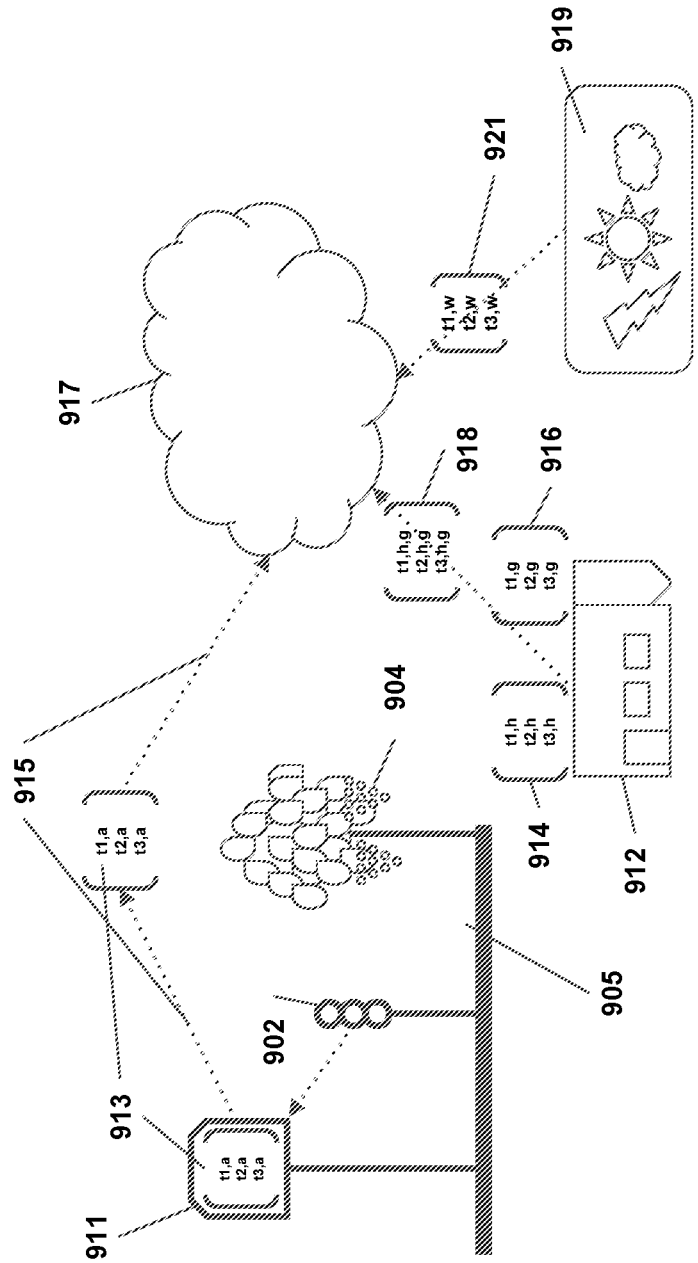
FIG. 9 is a schematic representation for data acquisition to create a synthetic sensor based on an unknown signal, in accordance with at least some embodiments described herein.

In FIG. 9, the data acquisition portion of a machine learning driven sensor fusion system for sensing an unknown signal is implemented, in an embodiment. An array of gas and air quality sensors 902 is installed at a specific geographical location 905. Periodically, grapes are harvested 904 from this specific geographical location 905 and sent to a laboratory for testing 912. The time and date of harvest 914 and the laboratory testing result 916 are then transmitted to the cloud computing storage and processing facility 917 creating a snapshot time series data set of smoke taint 918. A data transfer device 911 gathers the time series sensor reading data 913 from the array of gas and air quality sensors 902. This data transfer device 911 then transfers the time series sensor reading data 913 via a network 915 to a cloud computing storage and processing facility 917. A weather data service 919 provides a feed of time series weather data 921 for the specific geographic location 905 to the cloud computing storage and processing facility 917.

Figure 10:
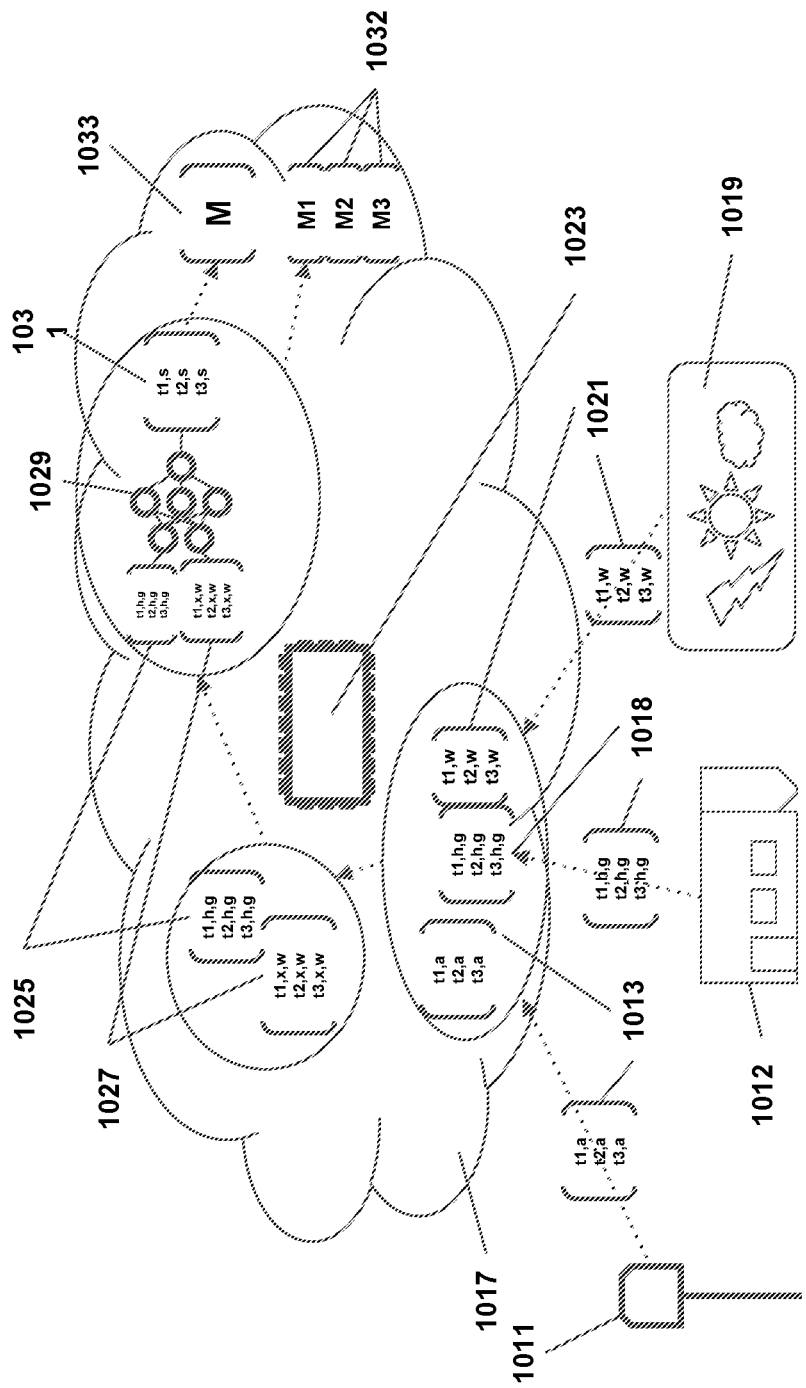
FIG. 10 is a schematic representation of the machine learning model to create a synthetic sensor for sensing an unknown signal, in accordance with at least some embodiments described herein.

In FIG. 10, the machine learning model creation portion of a machine learning driven sensor fusion system for sensing an unknown signal is implemented, in an embodiment. At a cloud computing storage and processing facility 1017, the cloud computing system 1023 receives the time series sensor reading data 1013 from the data transfer device 1011. The cloud computing system 1023 also receives the snapshot time series data of smoketaint 1018 from the testing laboratory 1012. The cloud computing system 1023 also receives the time series weather data 1021 from the weather data service 1019. The cloud computing system 1023 then creates a target data set 1025 using the snapshot time series data of smoketaint 1018. The cloud computing system 1023 then creates a feature data set 1027 by combining the time series sensor reading data 1013 and the time series weather data 1021. The target data set 1025 and the feature data set 1027 are then used to train a neural network 1029 to create a machine learning model 1031 for smoke taint. This machine learning model 1031 can now create synthetic sensor readings for smoke taint 1033, just using the time series sensor reading data contained in the feature data set 1027. A sensitivity analysis of the contributions of each type of time series sensor data 1013 to the performance of the machine learning model 1031 can be performed by retraining new machine learning models 1032 which each omit a single time series sensor data stream. The performance of each of these machine learning models with omitted data 1032 can then be compared to determine what sensors are needed to detect the signal which is a precursor to smoke taint. An agronomist or viticulturist could access the machine learning models 1032 on a computing device to view estimations of smoke taint, and make decisions about follow up testing.

Figure 11:
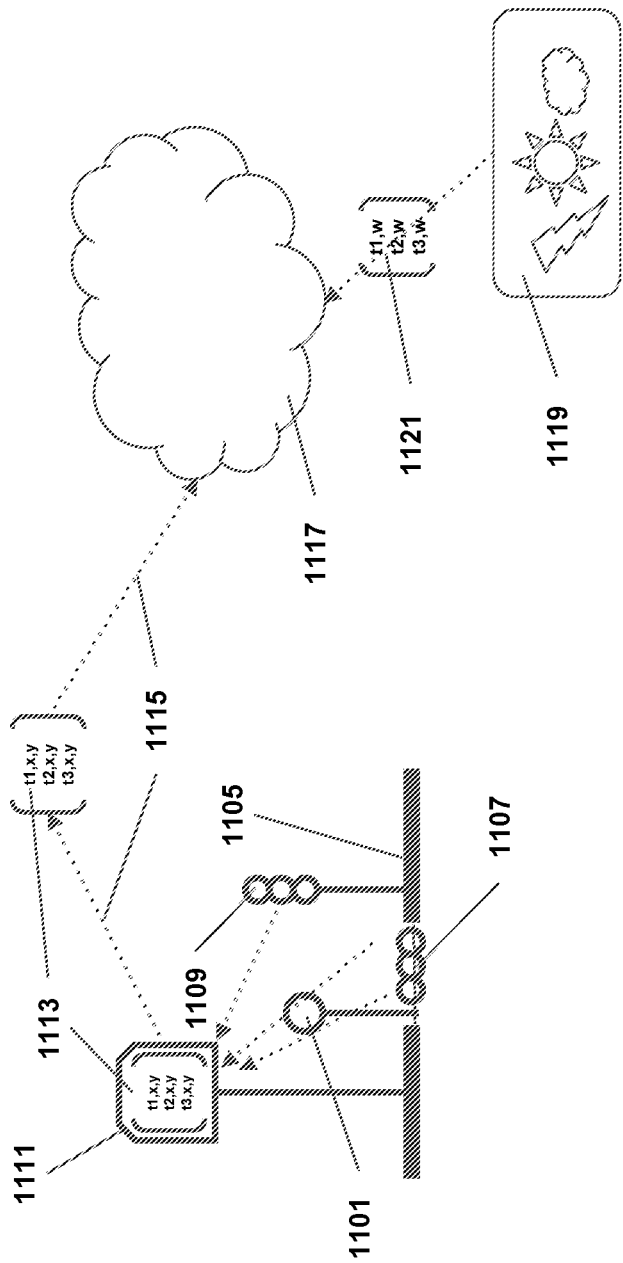
FIG. 11 a schematic representation for data acquisition to create a synthetic sensor for sensing soil-atmosphere gas flux, in accordance with at least some embodiments described herein.

In FIG. 11, the data acquisition portion of a machine learning driven sensor fusion system is implemented to create a synthetic sensor of soil gas flux, in an embodiment. A high quality, high cost eddy covariance sensor system 1101 is installed at a specific geographical location 1105. An array of soil gas sensors 1107 is also installed at this same specific geographical location 1105. Above this soil sensor array 1107 at this same specific geographical location 1105 an array of microclimate and air sensors 1109 is installed. A data transfer device 1111 gathers the time series sensor reading data 1113 from the eddy covariance sensor system 1101, array of soil gas sensors 1107, and the array of microclimate and air sensors 1109. This data transfer device 1111 then transfers the time series sensor reading data 1113 via a network 1115 to a cloud computing storage and processing facility 1117. A weather data service 1119 provides a feed of time series weather data 1121 for the specific geographic location 1105 to the cloud computing storage and processing facility 1117.

In FIG. 12, the machine learning model creation portion of a machine learning driven sensor fusion system is implemented to create a synthetic sensor of soil gas flux, in an embodiment. At a cloud computing storage and processing facility 1117, the cloud computing system 1210 receives the time series sensor reading data 1113 from the data transfer device 1111. The cloud computing system 1210 also receives the time series weather data 1121 from the weather data service 1119. The cloud computing system then separates the time series data sensor readings 1113 into a target data set 1230 of time series eddy covariance sensor system readings and a feature data set 1220 of time series soil gas array sensor data readings and time series microclimate and air array sensor data readings. The time series weather data 1121 is then added to the feature data set 1220 to create a complete feature data set. The target data set 1230 and the feature data set 1220 are then used to train a neural network 1230 to create a machine learning model 1235 for soil gas flux. This machine learning model 1235 can now create synthetic sensor readings for soil gas flux 1240, just using the time series data contained in the feature data set 1220. The machine learning mode 1235 can then be moved out of the cloud computing system 1210 and run on another device, including a mobile device 1250 or offline computer 1260 that has access to a feature data set 1220. An agronomist or viticulturist could then use the mobile device to view synthetic sensor readings of soil gas flux to make agronomic decisions to measure, manage, and reduce carbon and carbon equivalent gas emissions, or an offline computer could generate synthetic sensor readings to make automated agricultural decisions to manage and reduce carbon and carbon equivalent gas emissions.

The foregoing description is presented to enable one of ordinary skill in the art to make and use the disclosed embodiments and modifications thereof, and is provided in the context of a patent application and its requirements. Various modifications to the disclosed embodiments and the principles and features described herein will be readily apparent to those of ordinary skill in the art. Thus, the present disclosure is not intended to limit the invention to the embodiments shown; rather, the invention is to be accorded the widest scope consistent with the principles and features described herein.

What is claimed is:

1. A method of generating a synthetic sensor for providing an agricultural measurement comprising:
   receiving a plurality of secondary signals from a plurality of secondary sensors;
   downloading a trained learning model on a processor enabled device,
      wherein the trained learning model is configured to transform the plurality of secondary signals into a value of a primary signal for the agricultural measurement,
      wherein the trained learning model is trained by obtaining a measured value of the primary signal for the agricultural measurement from at least one primary sensor and training the trained learning model by modeling the plurality of secondary signals to the measured value of the primary signal of the agricultural measurement; and
   transforming the plurality of secondary signals into the value of the primary signal for displaying on the processor enabled device,
   wherein the plurality of secondary sensors is used to measure at least one of soil volumetric moisture, soil tension, soil temperature, air humidity, air temperature, and barometric pressure, and the primary signal is a value of soil matric potential.

2. The method according to claim 1, wherein a neural network is a recurrent neural network that is used to create the trained learning model that models a relationship between the plurality of secondary signals and the measured value of the primary signal.

3. The method according to claim 1, wherein the trained learning model is trained using secondary signals from at least five secondary sensors.

4. The method according to claim 1, wherein the value of the primary signal is a value measured by a sensor other than the plurality of secondary sensors.

5. The method according to claim 1, wherein the primary signal replaces one of the plurality of secondary signals.

6. The method according to claim 1 further comprising:
   obtaining at least one historical environmental data value; and
   predicting a future value of the primary signal based on the at least one historical environmental data value.

7. The method according to claim 6, wherein the at least one historical environmental data value is weather data.

8. A system for providing a synthetic sensor for agricultural measurements comprising:
   a plurality of secondary sensors configured to output a plurality of secondary signals;
   a trained learning model that is configured to transform the plurality of secondary signals into a value of a primary signal,
      wherein the trained learning model is trained by obtaining a measured value of the primary signal for the agricultural measurement from at least one primary sensor and training the trained learning model by modeling the plurality of secondary signals to the measured value of the primary signal of the agricultural measurement; and
   at least one device having a display that is configured to output the value of the primary signal that is a transformation of the plurality of secondary signals from the plurality of secondary sensors by the trained learning model,
      wherein the trained learning model is downloaded on the at least one device,
      wherein the plurality of secondary sensors is used to measure at least one of soil volumetric moisture, soil tension, soil temperature, air humidity, air temperature, and barometric pressure, and the primary signal is a value of soil matric potential.

9. The system of claim 8, wherein the value of the primary signal is a value measured by a sensor other than the plurality of secondary sensors.

10. The system of claim 8, wherein the primary signal replaces one of the plurality of secondary signals.

* * * * *